(12) United States Patent
Preiss-Bloom et al.

(10) Patent No.: US 12,702,443 B2
(45) Date of Patent: Aug. 11, 2026

(54) SUBCHONDRAL BONE DEFECT TREATMENT

(71) Applicant: OSSIO Ltd, Caesarea (IL)

(72) Inventors: Orahn Preiss-Bloom, Zichron Yaakov (IL); Brian J. Cole, Chicago, IL (US)

(73) Assignee: OSSIO Ltd, Caesarea (IL)

( * ) Notice: Subject to any disclaimer, the term of this patent is extended or adjusted under 35 U.S.C. 154(b) by 191 days.

(21) Appl. No.: 18/596,933

(22) Filed: Mar. 6, 2024

(65) Prior Publication Data

US 2024/0299063 A1 Sep. 12, 2024

Related U.S. Application Data

(60) Provisional application No. 63/450,140, filed on Mar. 6, 2023.

(51) Int. Cl.
*A61B 17/56* (2006.01)

(52) U.S. Cl.
CPC .................................. *A61B 17/562* (2013.01)

(58) Field of Classification Search
CPC ....... A61B 17/86; A61B 17/866; A61B 17/56; A61B 17/562; A61B 17/84; A61B 17/846
See application file for complete search history.

(56) References Cited

U.S. PATENT DOCUMENTS 5,306,311 A * 4/1994 Stone ........................ C08L 1/00 623/14.12
9,717,544 B2 8/2017 Sharkey et al.
9,730,744 B2 8/2017 Sharkey et al.
9,775,639 B2 10/2017 Hanson et al.
2007/0244484 A1* 10/2007 Luginbuehl ............. A61L 27/56 606/86 R
2011/0054609 A1* 3/2011 Cook .................. A61F 2/30756 623/13.12
2020/0246148 A1* 8/2020 Gelse ........................ A61F 2/28

FOREIGN PATENT DOCUMENTS

WO 2016035088 A1 3/2016
WO 2016035089 A1 3/2016
WO 2016103049 A1 6/2016
WO 2017155956 A1 9/2017
WO 2018002917 A1 1/2018
WO 2019049062 A1 3/2019
(Continued)

OTHER PUBLICATIONS

U.S. Appl. No. 63/450,140, filed Mar. 6, 2023.

*Primary Examiner* — Christopher J Beccia
(74) *Attorney, Agent, or Firm* — Ballard Spahr LLP

(57) ABSTRACT

Apparatus and methods are described for treating a subchondral bone defect within a bone of a subject that is adjacent to a joint. A hole is created within the bone extending from a first cortex of the bone to a second cortex of the bone. An implantable device is inserted into the hole such that the implantable device extends from the first cortex of the bone through the subchondral defect and to the second cortex of the bone, the implantable device having a flexural modulus of more than 10 GPa and being resorbable. The implantable device is left deployed within the bone, such that the implantable device becomes resorbed into the bone. Other applications are also described.

20 Claims, 4 Drawing Sheets

(56) References Cited

FOREIGN PATENT DOCUMENTS

| | | | |
|---|---|---|---|
| WO | 2019123462 | A1 | 6/2019 |
| WO | 2020044327 | A1 | 3/2020 |
| WO | 2023002471 | A1 | 1/2023 |
| WO | 2023100173 | A1 | 6/2023 |
| WO | 2024105655 | A1 | 5/2024 |

* cited by examiner

SUBCHONDRAL BONE DEFECT TREATMENT

CROSS-REFERENCES TO RELATED APPLICATIONS

The present application claims the benefit of U.S. Provisional Patent Application No. 63/450, 140 to Preiss-Bloom, filed Mar. 6, 2023, entitled “Subchondral bone defect treatment,” which is incorporated herein by reference.

FIELD OF EMBODIMENTS OF THE INVENTION

The present invention relates to medical apparatus and methods, and specifically to apparatus and methods for treating subchondral bone damage.

BACKGROUND

Structural damage to bone can cause injury, trauma, degeneration or erosion of otherwise healthy tissue. The resultant damage can be characterized as a bone defect that can take the form of a fracture, lesion, edema, tumor, or sclerotic hardening, by way of example. Particularly in joints, the damage may not be limited to a bone defect, and may also include cartilage loss (especially articular cartilage), tendon damage, and inflammation in the surrounding area.

Various surgical and non-surgical treatments are utilized to reduce or eliminate pain and restore joint function. To this end, there have been injectable or fillable hardening materials such as bone cements, bone void fillers, or bone substitute materials that have been used to stabilize bone defects.

SUMMARY OF EMBODIMENTS

For any implantable device placed near a bone joint, where a combination of forces are acting upon the area to be treated, the biomechanical risks of introducing a material having different physical properties than naturally occurring bone are unknown. An implantable device should mimic naturally occurring bone in both its biomechanical and physiological functions as well as its biological properties. Accordingly, it is desirable to provide implantable devices that can provide mechanical strength and structural integrity to the area to be treated, while also being as physiologically and biologically compatible as possible to reduce or eliminate any potential negative effects to the patient. It is desirable to provide implantable devices that are configured for the treatment or repair of damaged bone tissue particularly at the joints, and even more particularly at the subchondral bone level. To this end, there have been injectable or fillable hardening materials such as bone cements, bone void fillers, or bone substitute materials that have been used to stabilize bone defects. However, there has not previously been a structural fixation device that can reinforce the bone defect by bridging through the bone defect by extending from a bone cortex on one side of the defect to a bone cortex on the other side of the defect.

In accordance with some applications of the present invention, methods, apparatus and instruments are provided for treating joint pain to restore natural joint function and preserve the joint’s articular and cartilage surface. In particular, the apparatus and methods described herein are applied to bone defects, such as bone marrow lesions, edema, fissures, fractures, hardened bone, etc. near the joint surface, which can lead to a mechanical disadvantage and abnormal stress distribution in the periarticular bone, causing inflammation and generating pain. In such cases, treatment that are applied through the joint that violate the articular and cartilage surface often weaken the bone and have unpredictable results. Typically, the apparatus and methods described herein treat pain at its source, within the subchondral region of a bone of a joint, in order to relieve the pain.

In accordance with some applications of the present invention, an implantable device (e.g., a pin, a screw, a rod, a nail, and/or a bar) is inserted through a subchondral bone defect, such that the device passes through bone cortexes on each side of the defect. The implantable device is typically implanted to treat damaged bone tissue particularly at the joints, and even more particularly at the subchondral bone level. The implantable device is configured to provide mechanical strength and structural integrity to bone tissue to be treated, while also being physiologically and biologically compatible. Typically, the implantable device has a flexural modulus of more than 10 Gpa (e.g., more than 15 GPa) and/or less than 30 GPa, e.g., 10-30 GPa or 15-30 GPA. The implantable device is typically configured for the treatment or repair of damaged bone tissue at the joints, and even more particularly at the subchondral bone level. By reinforcing the periarticular bone, the implantable device typically changes the structural integrity of the affected bone and restores normal healing function, thus leading to a resolution of the inflammation surrounding the defect. Typically, the implantable device is formed of a resorbable material, such that once the bone has healed, the device is resorbed into the natural tissue. The implantable device may also be formed of bone material, such as allograft material. Typically, the implantable device includes a resorbable material that includes osteoconductive minerals, which are configured to support bone regrowth and regeneration.

Typically, the apparatus and methods described herein are configured to treat damaged bone tissue particularly at the joints, and more particularly at the subchondral bone level, by mechanically strengthening and/or stabilizing the defect, and biologically initiating or stimulating a healing response to the defect. The implantable device is typically sufficiently strong (e.g., by having a flexural modulus of 10-30 GPa or 15-30 GPA) and is structurally positioned within the bone in a sufficiently strong manner (e.g., by being implanted such that the device passes through bone cortexes on each side of the defect), such that the implantable device provides mechanical strength to bone tissue to be treated. Typically, the implantable device is left deployed within the bone, subsequent to the procedure (i.e., the incision in the subject skin via which the implantable device is inserted into the bone is closed, with the implantable device remaining deployed within the bone). Further typically, during its deployment, the implantable device promotes healing of the subchondral defect. Still further typically, after a given time (by which point, the subchondral defect has typically healed), the implantable device is resorbed into the bone.

Typically, the apparatus and methods described herein are intended to both strengthen the bone and stimulate the bone. Bone fractures or non-unions are typically stabilized, integrated or healed, which results in reduction of a bone defect, such as a bone marrow lesion or edema. Further typically, the apparatus and methods described herein restore and/or alter the distribution of forces in a joint to thereby relieve pain.

In the context of the present applications, including in the claims, the term "subchondral bone defect" should be interpreted as including any subchondral bone defect, including but not limited to a fracture, a lesion, edema, a tumor, and/or sclerotic hardening, by way of example.

There is therefore provided, in accordance with some applications of the present invention, a method for treating a subchondral bone defect within a bone of a subject that is adjacent to a joint, the method including:

- creating a hole within the bone extending from a first cortex of the bone to a second cortex of the bone;
- inserting an implantable device into the hole such that the implantable device extends from the first cortex of the bone through the subchondral defect and to the second cortex of the bone, the implantable device having a flexural modulus of more than 10 GPa and being resorbable; and
- leaving the implantable device deployed within the bone, such that the implantable device becomes resorbed into the bone.

In some applications, the implantable device has a flexural modulus of more than 15 GPa.

In some applications, inserting the implantable device into the hole includes inserting the implantable device such that one side of the implantable device is anchored to a peripheral cortex, to thereby create a cantilever beam support.

In some applications, inserting the implantable device into the hole includes inserting, into the hole, an implantable device, selected from the group consisting of: a rod, a bar, a screw, a pin, and a nail.

In some applications, a span of a cross-sectional shape defined by the implantable device is 2 mm-10 mm.

In some applications, the bone includes a femur of the subject, and inserting the implantable device into the hole includes inserting the implantable device such that the implantable device extends from a lateral or medial cortex of the bone, through the subchondral defect, and to a condylar cortex.

In some applications, inserting the implantable device into the hole includes inserting the implantable device such that the implantable device is less than 30 mm above a subchondral plate.

In some applications, the bone includes a tibia of the subject, and inserting the implantable device into the hole includes inserting the implantable device such that the implantable device extends from a lateral cortex of the bone, through the subchondral defect, and to a medial cortex.

In some applications, inserting the implantable device into the hole includes inserting the implantable device such that the implantable device is less than 30 mm below a subchondral plate.

In some applications, the implantable device has a flexural modulus of 10-30 GPa.

In some applications, the implantable device has a flexural modulus of 15-30 GPa.

In some applications, the implantable device has an initial length of 50-150 mm.

In some applications, the method further includes trimming the implantable device prior to inserting the implantable device into the hole.

In some applications, the implantable device has an initial length of 70-120 mm.

In some applications, the implantable device has a polygonal cross-sectional shape.

In some applications, the implantable device has a hexagonal cross-sectional shape.

In some applications, the implantable device is composed of at least 30% mineral weight-by-weight.

In some applications, the implantable device includes reinforcing mineral fibers.

In some applications, the reinforcing mineral fibers include continuous fibers having lengths of 30-150 mm.

In some applications, inserting the device into the hole includes inserting the device into the hole such that a majority of the reinforcing fibers are aligned substantially in parallel to a surface of the joint.

In some applications, inserting the device into the hole includes inserting the device into the hole such that a majority of the reinforcing fibers are aligned substantially in parallel to the surface of the joint in a lateral-medial orientation of the joint.

In some applications, inserting the device into the hole includes inserting the device into the hole such that a majority of the reinforcing fibers are aligned substantially in parallel to the surface of the joint in a medial-lateral orientation of the joint.

In some applications, inserting the device into the hole includes inserting the device into the hole such that a majority of the reinforcing fibers pass through at least one of the first and second cortexes.

In some applications, inserting the device into the hole includes inserting the device into the hole such that a majority of the reinforcing fibers pass through both of the first and second cortexes.

In some applications, the implantable device defines an implantable device body and protrusions from the implantable device body, the protrusions being selected from the group consisting of: threads, ribs, and teeth.

In some applications, the protrusions have heights of 0.1-1 mm.

In some applications, the implantable device is hollow and defines a lumen therethrough.

In some applications, a diameter of the lumen is 1.0 mm-2.4 mm.

In some applications, the implantable device defines at least one fenestration extending from the lumen to outside the implantable device.

In some applications, the method further includes injecting one or more agents into the subchondral bone defect via the lumen and the fenestration of the implantable device.

In some applications, the implantable device defines 1-4 fenestrations around a circumference of the implantable device at any given location along its length at which it defines the fenestrations.

In some applications, the implantable device defines 1-40 fenestrations along a length of the of the implantable device at any given location around its circumference at which it defines such fenestrations.

There is further provided, in accordance with some applications of the present invention, an apparatus for treating a subchondral bone defect within a bone of a subject that is adjacent to a joint, the apparatus including:

- an implantable device configured to be inserted into a hole within the bone, such that the implantable device extends from a first cortex of the bone, through the subchondral defect, and to a second cortex of the bone,
- the implantable device having a flexural modulus of more than 10 GPa and being resorbable, and
- the implantable device comprising an implantable device body and protrusions from the implantable device body, the protrusions being selected from the group consisting of: threads, ribs, and teeth.

The present invention will be more fully understood from the following detailed description of applications thereof, taken together with the drawings, in which:

DETAILED DESCRIPTION OF EMBODIMENTS

Figure 1A:
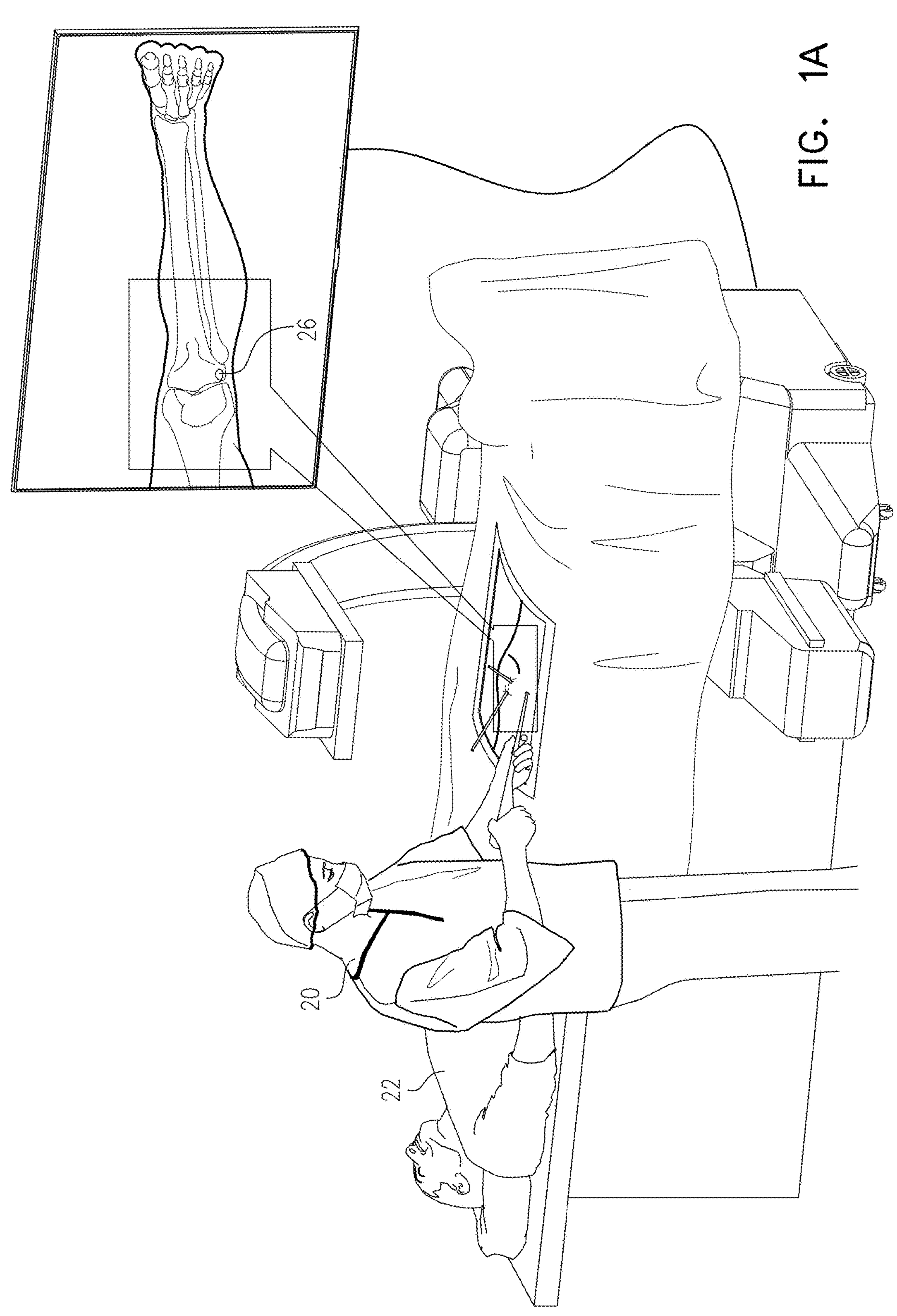
FIG. 1A is a schematic illustration of a cortex-to-cortex implant being implanted into a subject's knee, in accordance with some applications of the present invention.

Reference is now made to FIG. 1A, which is a schematic illustration of a physician 20 implanting a cortex-to-cortex implant in the knee of a subject 22 who is suffering from a subchondral bone defect 26, in accordance with some applications of the present invention. As described hereinabove, for any implantable device placed near a bone joint, where a combination of forces are acting upon the area to be treated, the biomechanical risks of introducing a material having different physical properties than naturally occurring bone are unknown. An implantable device should mimic naturally occurring bone in both its biomechanical and physiological functions as well as its biological properties. Accordingly, it is desirable to provide implantable devices that can provide mechanical strength and structural integrity to the area to be treated, while also being as physiologically and biologically compatible as possible to reduce or eliminate any potential negative effects to the patient. It is desirable to provide implantable devices that are configured for the treatment or repair of damaged bone tissue particularly at the joints, and even more particularly at the subchondral bone level. In accordance with some applications of the present invention, methods, apparatus and instruments are provided for treating joint pain to restore natural joint function and preserve the joint's articular and cartilage surface. In particular, the apparatus and methods described herein are applied to bone defects, such as bone marrow lesions, edema, fissures, fractures, hardened bone, etc. near the joint surface, which can lead to a mechanical disadvantage and abnormal stress distribution in the periarticular bone, causing inflammation and generating pain. In such cases, treatment that are applied through the joint that violate the articular and cartilage surface often weaken the bone and have unpredictable results. Typically, the apparatus and methods described herein treat pain at its source, within the subchondral region of a bone of a joint, in order to relieve the pain.

In accordance with some applications of the present invention, an implantable device 24 (e.g., a pin, a screw, a nail, a rod, and/or a bar, shown in FIGS. 2A-4) is inserted through a subchondral bone defect, such that the device passes through bone cortexes on each side of the defect. The implantable device is typically implanted to treat damaged bone tissue particularly at the joints, and even more particularly at the subchondral bone level. The implantable device is configured to provide mechanical strength and structural integrity to bone tissue to be treated, while also being physiologically and biologically compatible. Typically, the implantable device has a flexural modulus of more than 10 Gpa (e.g., more than 15 GPa) and/or less than 30 GPa, e.g., 10-30 GPa or 15-30 GPA. The implantable device is typically configured for the treatment or repair of damaged bone tissue at the joints, and even more particularly at the subchondral bone level. By reinforcing the periarticular bone, the implantable device typically changes the structural integrity of the affected bone and restores normal healing function, thus leading to a resolution of the inflammation surrounding the defect. Typically, the implantable device is formed of a resorbable material, such that once the bone has healed, the device is resorbed into the natural tissue. The implantable device may also be formed of bone material, such as allograft material. Typically, the implantable device includes a resorbable material that includes osteoconductive minerals, which are configured to support bone regrowth and regeneration.

Typically, the apparatus and methods described herein are configured to treat damaged bone tissue particularly at the joints, and more particularly at the subchondral bone level, by mechanically strengthening and/or stabilizing the defect, and biologically initiating or stimulating a healing response to the defect. The implantable device is typically sufficiently strong (e.g., by having a flexural modulus of 10-30 GPa or 15-30 GPA) and is structurally positioned within the bone in a sufficiently strong manner (e.g., by being implanted such that the device passes through bone cortexes on each side of the defect), such that the implantable device provides mechanical strength to bone tissue to be treated. Typically, the implantable device is left deployed within the bone, subsequent to the procedure (i.e., the incision in the subject skin via which the implantable device is inserted into the bone is closed, with the implantable device remaining deployed within the bone). Further typically, during its deployment, the implantable device promotes healing of the subchondral defect. Still further typically, after a given time (by which point, the subchondral defect has typically healed), the implantable device is resorbed into the bone.

Typically, the apparatus and methods described herein are intended to both strengthen the bone and stimulate the bone. Bone fractures or non-unions are typically stabilized, integrated or healed, which results in reduction of a bone defect, such as a bone marrow lesion or edema. Further typically, the apparatus and methods described herein restore and/or alter the distribution of forces in a joint to thereby relieve pain.

For some applications, the procedure described herein is performed arthroscopically or percutaneously to treat pain by stabilizing chronic stress fracture, resolving any chronic bone marrow lesion or edema. The procedure typically comprises evaluating a joint, for example, by taking an image of the joint, detecting the presence of one or more subchondral defects, diagnosing which of these subchondral defects is the source of pain, and determining an extent of treatment for the subchondral defect. Typically, the apparatus and methods described herein are applicable to both chronic defects and injuries, as well as acute injuries.

For some applications, detection and identification of a relevant bone marrow lesion or bone marrow edema is achieved by imaging (e.g., magnetic resonance imaging (MRI), computed tomography (CT) and/or X-ray), manual palpation, and/or chemical or biological assay. MRI imaging is typically used. For some applications, a T1-weighted MRI is used to detect sclerotic bone, for example. For some applications, a T2-weighted MRI is used to detect lesions, edemas, and/or cysts.

Typically, the implantable device is inserted through a bone defect and passes through at least one bone cortex on the side of the defect. Further typically, the implantable device passes through two bone cortexes, one on each side of the defect, to mechanically strengthen the subchondral bone in the region of the bone marrow lesion or defect.

For some applications, the implantable device is implanted into the subchondral bone to provide mechanical support to the damaged or affected bone region, such as where an insufficiency fracture or stress fracture has occurred. Typically, the implantable device improves load distribution in the subchondral region. For some applications, the implantable device is implanted into the femur and/or the tibia, and is configured to support tibio-femoral compressive loads within the knee. For some applications, the implantable device integrates sclerotic bone with the surrounding healthy bone tissue. The implantable device is typically configured as a bi-cortical bone implant (i.e., a cortex-to-cortex implant that passes through bone cortexes on each side of the defect). For some applications, one side of the implantable device is anchored to the peripheral cortex to create a cantilever beam support (i.e., a portion of the implant is inserted into bone but the second end stays outside or near the outer surface of the bone).

Figure 1B:
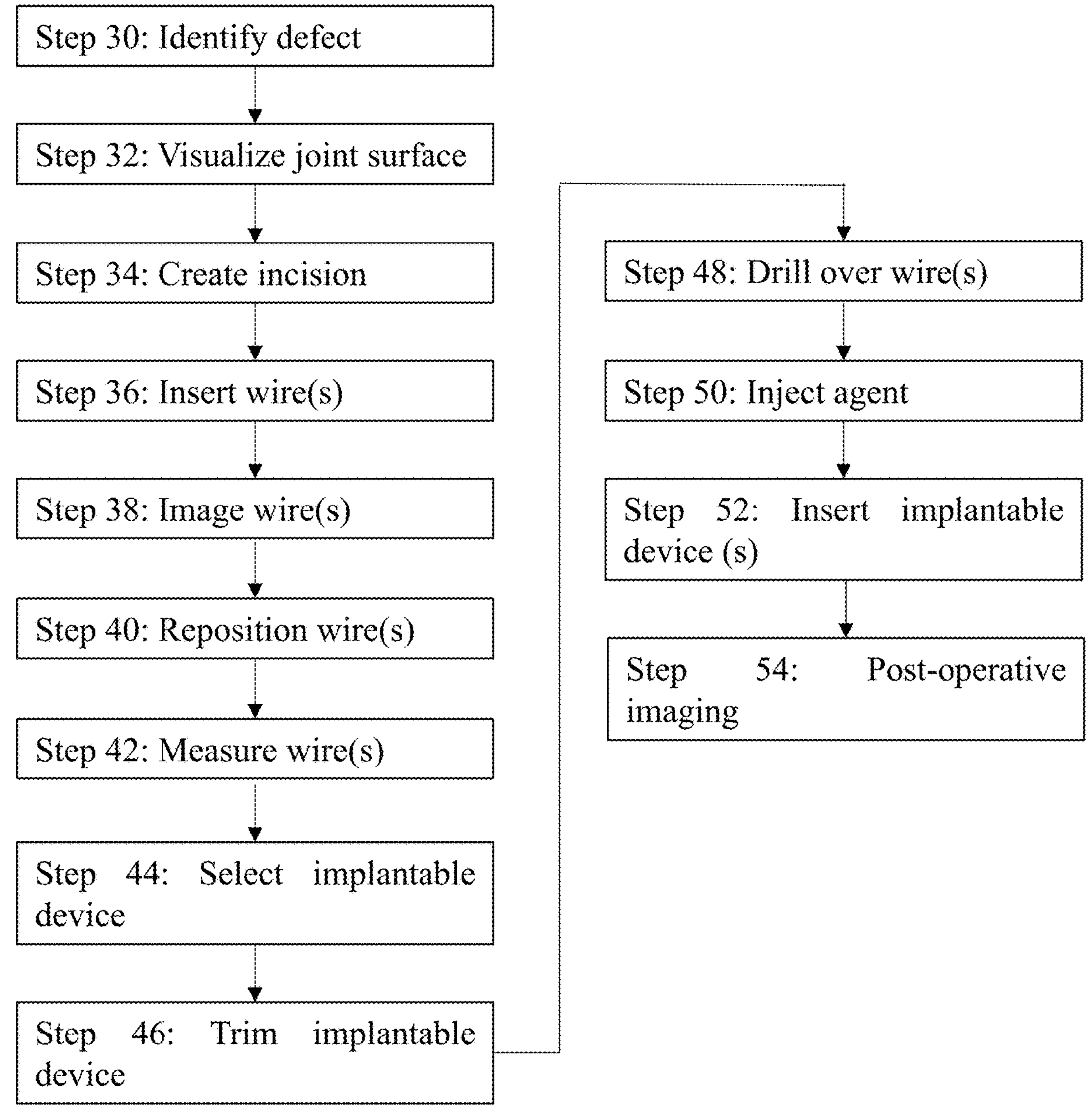
FIG. 1B is a flowchart showing steps of a procedure that is performed on a subject suffering from a femoral and/or tibial subchondral bone defect, in accordance with some applications of the present invention.

Reference is now made to FIG. 1B, which is a flowchart showing steps of a procedure that is performed on a subject suffering from a femoral and/or tibial subchondral bone defect, in accordance with some applications of the present invention.

For some applications, in an initial step (step 30), a subchondral bone defect is identified, typically using MRI imaging. As described hereinabove, for some applications, a T1-weighted MRI is used to detect sclerotic bone. For some applications, a T2-weighted MRI is used to detect lesions, edemas, and cysts.

For some applications, an arthroscope is inserted through an arthroscopic portal into the joint space to visualize the joint surface (step 32).

Typically, a small incision is made in the skin to allow for insertion of the guide wire and implant (step 34).

Subsequently, in some applications, at least one guide wire (typically, a k-wire) is inserted percutaneously such that the wire enters into the medial or lateral cortex of the subchondral bone, passes through the bone defect, and exits through a second cortex, either on the opposite side of the subchondral bone or on the opposite site of the subchondral bone condyle (step 36). Typically, the wire is positioned such that the wire is distributed across the entire width of the subchondral bone defect. For some applications, a plurality of implantable devices are implanted into a single bone (e.g., as shown in FIGS. 2A-3B). Typically for such applications, a plurality of guide wires (e.g., two-four wires) are inserted through the bone, such that in a subsequent step a plurality of implantable devices are implanted over respective wires.

For some applications, the position of the wire is confirmed using a fluoroscope or other imaging methodology (step 38). For some applications, the wire is inserted under image intensification. Typically, the imaging is used to confirm that the wire passes from one cortex, through the bone defect, and then through a second cortex. Further typically, the imaging is used to confirm that the wire is distributed across the entire width of the subchondral bone defect. (As noted above, for some applications a plurality of wires are placed within a single bone.)

In some cases, one or more wires are repositioned as needed (step 40), on the basis of the imaging.

Typically, once the position of the wire is confirmed, the length of the wire is measured, typically using an indirect measuring device. For some applications, an over-the-wire depth gauge is inserted over the back of each wire to measure the length of the wire inserted into the bone (step 42).

For some applications, implantable device 24 is then selected such that the device matches the length of the wire inserted into the bone for each wire (step 44).

Typically, the initial length of the implantable device is more than 50 mm (e.g., more than 70 mm), and/or less than 150 mm (e.g., less than 120 mm), e.g., 50-150 mm, or 70-120 mm. For some applications, the implantable device is trimmed or cut to match the length of the wire that has been inserted into the bone (step 46).

Typically, a cannulated drill bit is used to drill over one of the guide wires such that the drill passes through the first cortex, through the bone defect, and then through the second cortex (step 48). Typically, the diameter of the hole that is drilled by the drill is smaller than the maximal diameter (or span) of the implantable device that will be inserted into the hole. For some applications, the implantable device is not circular and the drill hole diameter is smaller than one nominal cross-sectional spanning dimension of the implantable device but larger than another nominal cross-sectional spanning dimension. For some applications, the implantable device has a polygonal cross-sectional shape, such as a hexagonal cross-sectional shape. For some such applications, the drill hole diameter is larger than the edge-to-edge dimension of the hexagon but smaller than the corner-to-corner dimension.

Typically, the implantable device 24 has a substantially uniform diameter (or span) along the full length of the implantable device. (For some applications, the implantable device defines threads, ribs, teeth or other protrusions from the body of the implantable device. However, even in such cases, the diameter (or span) of the main body of the implantable device is typically substantially uniform along the full length of the implantable device.)

For some applications, subsequent to the hole having been drilled and prior to the implantable device being implanted, a chemical, biochemical and/or biological agent (such as Platelet Rich Plasma (PRP)), etc. is injected into the bone defect site at this stage (step 50). For some applications, this step is performed at a different point in the procedure. Alternatively or additionally, the implantable device is fenestrated and a chemical, biochemical and/or biological agent (such as Platelet Rich Plasma (PRP)), etc. is injected through the implant following implant insertion, as described in further detail hereinbelow.

Typically, the implantable device is inserted into the drill hole (step 52). For example, the implantable device is rotated into hole, or driven into hole. Typically, the implantable device is inserted into the drill hole by tamping the implantable device into the drill hole. Typically, the implantable device is implanted such that it enters into the medial or lateral cortex of the subchondral bone, passes through the bone defect, and exits through a second cortex, either on the opposite side of the subchondral bone or on the opposite site of the subchondral bone condyle. Typically, the implantable device is implanted such that it is distributed across the entire width of the subchondral bone defect.

Typically, in cases in which more than one wire has been inserted through the bone, steps 48 and 52 (and optionally step 50) are repeated for each of the wires, such that a respective implantable device is implanted over each one of the wires.

For some applications, post-operative imaging is performed (step 54). Typically, the implantable device is at least partially radio-translucent. Typically, the implanted device is therefore imaged using CT or MRI.

With respect to all of the steps described with reference to FIG. 1B, it is noted that at least some of these steps are optional and the order in which the steps are performed may be modified. The scope of the present disclosure includes performing only a portion of the described steps, and/or performing all or a portion of the steps in a different order to that presented in FIG. 1B, mutatis mutandis.

Figure 2A:
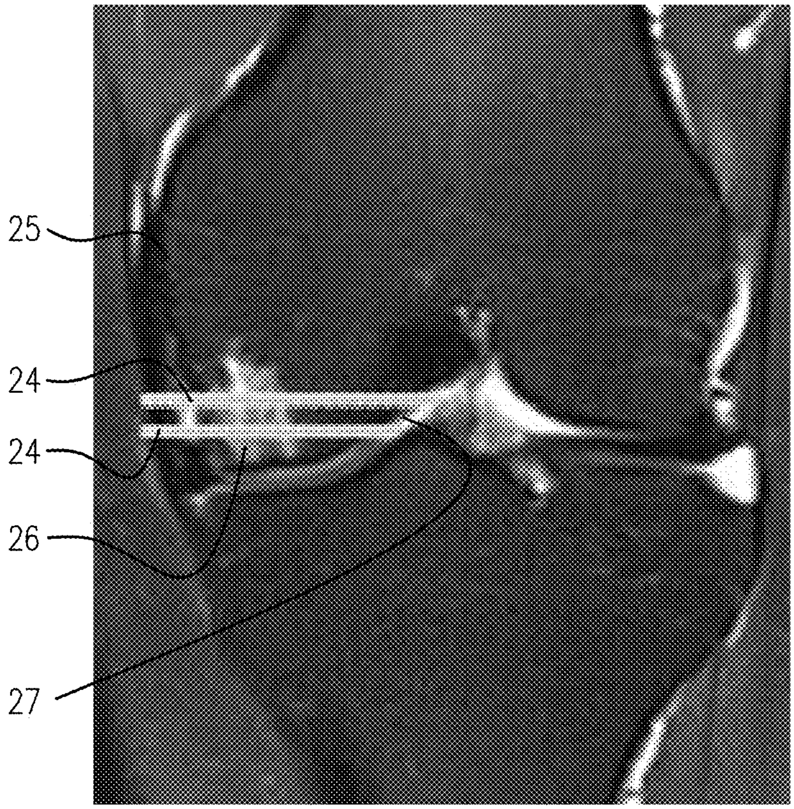
FIGS. 2A and 2B are schematic illustrations of cortex-to-cortex implants shown overlaid upon a transverse MRI slice showing the of a subject suffering from femoral subchondral bone defect, in accordance with some applications of the present invention.
Figure 2B:
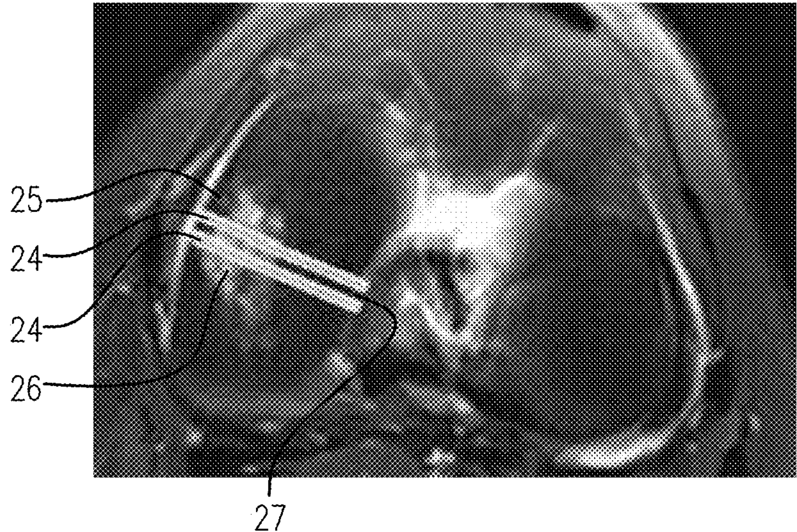
Figure 3:
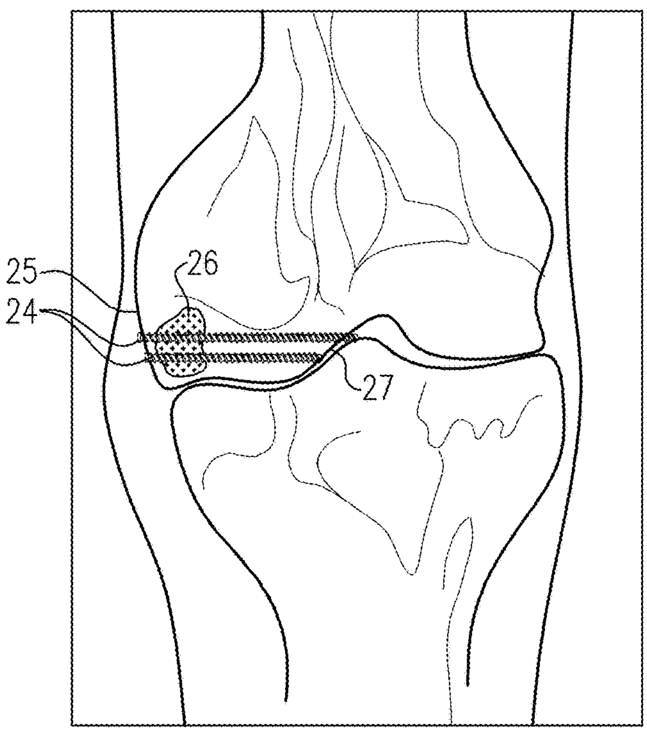
FIG. 3 is a schematic illustration of cortex-to-cortex implants implanted in the femur of a subject suffering from femoral subchondral bone defect, in accordance with some applications of the present invention.

Reference is now made to FIGS. 2A and 2B, which are schematic illustrations of cortex-to-cortex implantable devices 24 implanted in the femur 25 of subject 22, the subject suffering from femoral subchondral bone defect, in accordance with some applications of the present invention. Reference is also made to FIG. 3, which is a schematic illustration of cortex-to-cortex implantable devices 24 implanted in the femur 25 of subject 22, with the devices shown overlaid upon a transverse MRI slice, in accordance with some applications of the present invention. FIGS. 2A and 3 show a coronal slice of the subject's femur, while FIG. 2B shows an axial slice of the subject's femur. As shown, the subject is suffering from a subchondral bone defect 26. Such defects may include sclerotic bone, lesions, edemas, cysts, etc. Typically, the implantable device is implanted such that it enters into the medial or lateral cortex of the subchondral bone, passes through the bone defect, and exits from the condylar cortex 27 inside the knee (and typically in a non-weight bearing section of the knee). Typically, the implantable device is implanted such that it is distributed across the entire width of the subchondral bone defect. Typically, the implant is implanted into the femur such that is less than 30 mm (e.g., less than 20 mm, or less than 10 mm) above the subchondral plate. As shown, for some applications, two or more implantable devices are implanted within the bone that has subchondral defect.

Figure 4:
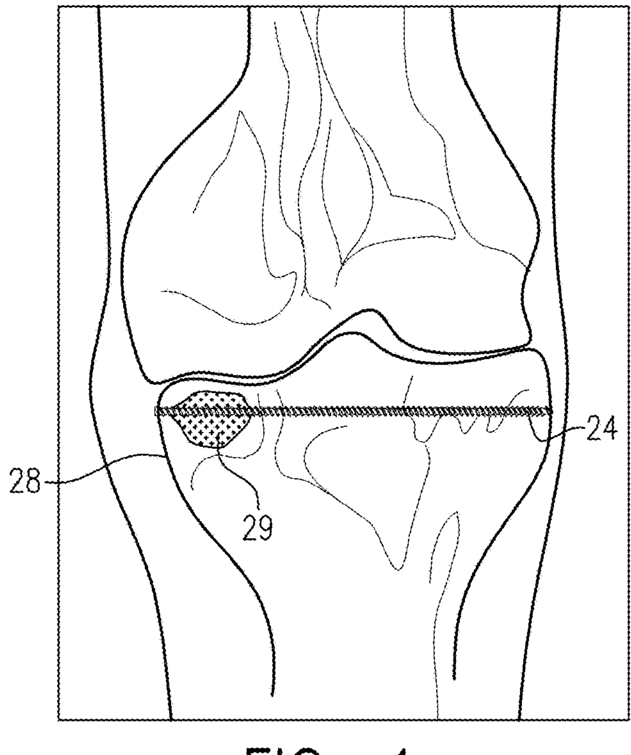
FIG. 4 is a schematic illustration of a cortex-to-cortex implant implanted in the tibia of a subject suffering from tibial subchondral bone defect, in accordance with some applications of the present invention.

Reference is now made to FIG. 4, which is a schematic illustration of cortex-to-cortex implantable device 24 implanted in the tibia 28 of subject 22, the subject suffering from a tibial subchondral bone defect, in accordance with some applications of the present invention. As shown, the subject is suffering from a subchondral bone defect 29. Such defects may include sclerotic bone, lesions, edemas, cysts, etc. Typically, the implantable device is implanted such that it enters into the medial cortex of the subchondral bone, passes through the bone defect, and exits from the lateral cortex, or vice versa. Typically, the implantable device is implanted such that it is distributed across the entire width of the subchondral bone defect. Typically, the implant is implanted into the tibia such that is less than 30 mm (e.g., less than 20 mm, or less than 10 mm) below the subchondral plate.

It is noted that although FIGS. 2A-4 show implantable device 24 being implanted within a subject's femur and/or a subject's tibia, the scope of the present disclosure includes implanting cortex-to-cortex implantable device 24 within bones of other joints that are suffering from subchondral defects, such as the hip joint, shoulder joint, elbow joint, ankle joint, metatarsal-phalangeal joint, thumb base joint (carpometacarpal joint), sacro-iliac joints, and/or spine joints, mutatis mutandis.

For some applications, the composition and/or structure of the implantable device 24 is generally similar to compositions described in one or more of the following patent applications, which are incorporated herein by reference:

US 2017/0246356 to Preiss-Bloom;
US 2017/0246355 to Preiss-Bloom;
US 2017/0281253 to Preiss-Bloom;
US 2019/0099522 to Preiss-Bloom;
US 2019/0282736 to Preiss-Bloom;
US 2020/00345895 to Preiss-Bloom;
US 2021/0137576 to Preiss-Bloom;
US 2021/0205505 to Preiss-Bloom;
US 2021/0369314 to Preiss-Bloom;
US 2022/0001081 to Preiss-Bloom;
US 2023/0024165to Preiss-Bloom; and
WO 23/002471 to Preiss-Bloom.

For some applications, implantable device 24 is formed of bone material, such as allograft material. Typically, implantable device 24 is formed of a resorbable material. Typically, the resorbable material has mineral content since the presence of osteoconductive minerals can help support bone regrowth and regeneration. Typically, the resorbable material is at least 30% mineral weight-by-weight by composition, e.g., at least 40%. Typically, mineral content of implantable device 24 is in the range of 40-70%, e.g., 40-60% weight-by-weight. Further typically, mineral content of implantable device 24 is in the form of reinforcing mineral fibers. Still further typically, implantable device 24 is formed of mineral fiber-reinforced biocomposite.

As described hereinabove, typically, implantable device 24 is formed of mineral fiber-reinforced biocomposite. For some applications, the reinforcing fibers are continuous fibers, typically in the range of 30-150 mm of length, e.g., in the range of 40-100 mm of length. Typically, a majority of the reinforcing fibers are aligned with the longitudinal axis of the implant. For some applications, the implantable device is configured such that, upon implantation, a majority (e.g., at least 70%, 80%, or 90%) of the reinforcing fibers are aligned substantially in parallel to surface of the joint in which the implantable device is implanted. For some applications, the implantable device is configured such that, upon implantation, a majority (e.g., at least 70%, 80%, or 90%) of the reinforcing fibers are more closely oriented in the lateral-medial or medial-lateral orientation of the joint (as opposed to the anterior-posterior). For some applications, the implantable device is configured such that, upon implantation, a majority (e.g., at least 70%, 80%, or 90%) of the continuous reinforcing fibers pass entirely through the bone defect and at least one bone cortex. Typically, the implantable device is configured such that, upon implantation, a majority (e.g., at least 70%, 80%, or 90%) of the continuous reinforcing fibers pass through two bone cortexes.

For some applications, implantable device 24 is formed of a magnesium alloy.

For some applications, implantable device 24 is a rod, a bar, a screw, a pin, and/or a nail.

In accordance with respective applications, the cross-sectional geometry of implantable device 24 is triangular, circular, ovular, square, pentagonal, hexagon, or octagonal. Typically, the cross-sectional geometry of the implantable device is not circular. Further typically, the cross-sectional geometry of the implantable device is a hexagon.

As described hereinabove, typically, the length of the implantable device is more than 50 mm (e.g., more than 70 mm), and/or less than 150 mm (e.g., less than 120 mm), e.g., 50-150 mm, or 70-120 mm. For some applications, the implantable device is trimmed or cut to match the length of the wires that are inserted into the bone. For some applications, the length of the implantable device is more than 40 mm, and/or less than 100 mm, e.g., 40-100 mm.

For some applications, the diameter of implantable device 24 is more than 2 mm (e.g., more than 3 mm, or more than 4 mm) and/or less than 10 mm (e.g., less than 6 mm, or less than 5 mm), e.g., 2 mm-10 mm, 3 mm-6 mm, or 4-5 mm. For some applications, the implantable device has a non-circular cross-sectional shape. For such cases, the span of the cross-sectional shape (i.e., the maximum distance measured across the cross-sectional shape) is typically more than 2 mm (e.g., more than 3 mm, or more than 4 mm) and/or less than 10 mm (e.g., less than 6 mm, or less than 5 mm), e.g., 2 mm-10 mm, 3 mm-6 mm, or 4-5 mm.

For some applications, the implantable device defines threads, ribs, teeth or other protrusions from the body of the implantable device. For some such applications, the height of the threads, ribs, teeth, or other protrusions is more than 0.1 mm (e.g., more than 0.2 mm) and/or less than 1 mm (e.g., less than 0.5 mm), e.g., 0.1-1 mm or 0.2-0.5 mm.

Typically, implantable device 24 is hollow and defines a lumen therethrough. For some applications, the diameter of the lumen is more than 1.0 mm (e.g., more than 1.2 mm) and/or less than 2.4 mm (e.g., less than 2.0 mm, or less than 1.6 mm), e.g., 1.0 mm-2.4 mm, 1.2-2.0 mm, or 1.2-1.6 mm.

As described hereinabove, for some applications, implantable device is inserted using a guide wire. For some applications, the guide wire has a diameter of more than 1.0 mm (e.g., more than 1.4 mm) and/or less than 2.5 mm (e.g., less than 1.6 mm), e.g., 1.0 mm-2.5 mm or 1.4 mm-1.6 mm.

For some applications, the subchondral bone region of a subject is stimulated to trigger or improve the body's natural healing process. For some such applications, one or more holes are drilled within the region of the defect to increase stimulation (e.g., blood flow, cellular turnover, etc.) and initiate a healing response leading to bone repair. For some applications, after holes are drilled, an osteogenic, osteoinductive, or osteoconductive agent is introduced to the site. Additionally or alternatively, chemical, biochemical and/or biological agents (such as Platelet Rich Plasma (PRP)), etc. are injected into the bone defect and/or the treatment site. Typically, such agents are introduced through the implant, around the implant, and/or apart from the implant but at the affected bone region, such as into the lower region of a bone marrow lesion or below the lesion.

For some applications, implantable device 24 is used as a portal to inject osteogenic, osteoinductive, osteoconductive, chemical, biochemical and/or biological agents (such as Platelet Rich Plasma (PRP)), etc. into the subchondral bone region. For some such applications, implantable device 24 is fenestrated and is hollow and defines a lumen therethrough. Typically, the implantable device is fenestrated with fenestrations (i.e., holes) of sufficient diameter to allow for injection of an osteogenic, osteoinductive, osteoconductive, chemical, biochemical and/or biological agents (such as Platelet Rich Plasma (PRP)), etc. through the lumen of the implant, out through the fenestrations into the surrounding bone defect area. Typically, the implantable device defines 1-4 fenestrations (e.g., 1-2 fenestrations) around the circumference of the implantable device at any given location along its length at which it defines such fenestrations. Typically, the implantable device defines 1-40 fenestrations (e.g., 2-20 fenestrations) along the length of the of the implantable device at any given location around its circumference at which it defines such fenestrations.

As noted above, in the context of the present applications, including in the claims, the term "subchondral bone defect" should be interpreted as including any subchondral bone defect, including but not limited to a fracture, a lesion, edema, a tumor, and/or sclerotic hardening, by way of example.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for treating a subchondral bone defect within a bone of a subject that is adjacent to a joint, the method comprising:

creating a hole within the bone extending from a first cortex of the bone to a second cortex of the bone;

inserting an implantable device into the hole such that the implantable device extends from the first cortex of the bone through the subchondral defect and to the second cortex of the bone, the implantable device having a flexural modulus of more than 10 GPa and being resorbable; and leaving the implantable device deployed within the bone, such that the implantable device becomes resorbed into the bone.

2. The method according to claim 1, wherein inserting the implantable device into the hole comprises inserting the implantable device such that one side of the implantable device is anchored to a peripheral cortex, to thereby create a cantilever beam support.

3. The method according to claim 1, wherein inserting the implantable device into the hole comprises inserting, into the hole, an implantable device, selected from the group consisting of: a rod, a bar, a screw, a pin, and a nail.

4. The method according to claim 1, wherein a span of a cross-sectional shape defined by the implantable device is 2 mm-10 mm.

5. The method according to claim 1, wherein the bone includes a femur of the subject, and wherein inserting the implantable device into the hole comprises inserting the implantable device such that the implantable device extends from a lateral or medial cortex of the bone, through the subchondral defect, and to a condylar cortex.

6. The method according to claim 5, wherein inserting the implantable device into the hole comprises inserting the implantable device such that the implantable device is less than 30 mm above a subchondral plate.

7. The method according to claim 1, wherein the bone includes a tibia of the subject, and wherein inserting the implantable device into the hole comprises inserting the implantable device such that the implantable device extends from a lateral cortex of the bone, through the subchondral defect, and to a medial cortex.

8. The method according to claim 7, wherein inserting the implantable device into the hole comprises inserting the implantable device such that the implantable device is less than 30 mm below a subchondral plate.

9. The method according to claim 1, wherein the implantable device has a flexural modulus of 10-30 GPa.

10. The method according to claim 1, wherein the implantable device has an initial length of 50-150 mm.

11. The method according to claim 1, wherein the implantable device has a polygonal cross-sectional shape.

12. The method according to claim 1, wherein the implantable device is composed of at least 30% mineral weight-by-weight.

13. The method according to claim 12, wherein the implantable device comprises reinforcing mineral fibers.

14. The method according to claim 13, wherein the reinforcing mineral fibers comprise continuous fibers having lengths of 30-150 mm.

15. The method according to claim 14, wherein inserting the device into the hole comprises inserting the device into the hole such that a majority of the reinforcing fibers are aligned substantially in parallel to a surface of the joint.

16. The method according to claim 14, wherein inserting the device into the hole comprises inserting the device into the hole such that a majority of the reinforcing fibers pass through at least one of the first and second cortexes.

17. The method according to claim 16, wherein inserting the device into the hole comprises inserting the device into the hole such that a majority of the reinforcing fibers pass through both of the first and second cortexes.

18. The method according to claim 1, wherein the implantable device defines an implantable device body and protrusions from the implantable device body, the protrusions being selected from the group consisting of: threads, ribs, and teeth.

19. The method according to claim 1, wherein the implantable device is hollow and defines a lumen therethrough.

20. An apparatus for treating a subchondral bone defect within a bone of a subject that is adjacent to a joint, the apparatus comprising:

an implantable device configured to be inserted into a hole within the bone, such that the implantable device extends from a first cortex of the bone, through the subchondral defect, and to a second cortex of the bone, the implantable device having a flexural modulus of more than 10 GPa and being resorbable, and the implantable device comprising an implantable device body and protrusions from the implantable device body, the protrusions being selected from the group consisting of: threads, ribs, and teeth.

* * * * *